US011050094B1

(12) United States Patent
Dai et al.

(10) Patent No.: US 11,050,094 B1
(45) Date of Patent: Jun. 29, 2021

(54) MOLTEN SALT COMPOSITIONS WITH ENHANCED HEAT TRANSFER AND REDUCED CORROSION PROPERTIES

(71) Applicant: UT-Battelle, LLC, Oak Ridge, TN (US)

(72) Inventors: Sheng Dai, Knoxville, TN (US); Carter W. Abney, Califon, NJ (US); Richard T. Mayes, Knoxville, TN (US); Dmitriy Dolzhnikov, Oak Ridge, TN (US); Huimin Luo, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 204 days.

(21) Appl. No.: 16/039,770

(22) Filed: Jul. 19, 2018

Related U.S. Application Data

(60) Provisional application No. 62/534,937, filed on Jul. 20, 2017.

(51) Int. Cl.
| | |
|---|---|
| *H01M 10/39* | (2006.01) |
| *C07D 307/68* | (2006.01) |
| *G21C 3/54* | (2006.01) |
| *G21C 1/02* | (2006.01) |
| *G21C 11/06* | (2006.01) |

(52) U.S. Cl.
CPC ........ *H01M 10/399* (2013.01); *C07D 307/68* (2013.01); *G21C 1/02* (2013.01); *G21C 3/54* (2013.01); *G21C 11/06* (2013.01)

(58) Field of Classification Search
CPC ... G21C 7/00; G21C 7/22; G21C 7/24; G21C 19/31; G21C 3/54; G21C 7/10; G21C 9/00; G21C 9/02; G21C 1/02; G21C 11/06; G21C 15/257; Y02E 30/38; C22B 1/00; C07D 307/68; C07D 307/56; H01M 10/399
USPC ........................................................ 429/103
See application file for complete search history.

(56) References Cited

U.S. PATENT DOCUMENTS

| | | | | |
|---|---|---|---|---|
| 2016/0232993 | A1* | 8/2016 | Kurina | G21C 3/58 |
| 2017/0263943 | A1* | 9/2017 | Li | C23C 16/18 |
| 2018/0075931 | A1* | 3/2018 | Arafat | G21C 1/03 |

OTHER PUBLICATIONS

Gimenez-Gavarrell P. et al., "Latent heat of fusion and melting temperature of molten salt based carbon nanotube suspensions used as phase change materials", Proceedings of the ASME 2015 9th International Conference on Energy Sustainability (Jun. 28-Jul. 2, 2015), San Diego, California, 5 pages.
Grimes W.R. "Molten-Salt Reactor Chemistry", Nuclear Applications and Technology (1970), 8(2), pp. 137-155 DOI: 10.13182/NT70-A28621.
Jo B. et al., "Enhanced Specific Heat Capacity of Molten Salt-Based Carbon Nanotubes Nanomaterials" Journal of Heat Transfer (Sep. 2015), vol. 137, pp. 091013-1-091013-7.
Leblanc D. "Molten salt reactors: A new beginning for an old idea", Nuclear Engineering and Design (2010), 240, pp. 1677-1656 doi:10.1016/j.nucengdes.2009.12.033.
Le Brun C. "Molten salts and nuclear energy production", Journal of Nuclear Materials (2007), 360, pp. 1-5 doi:10.1016/j.jnucmat.2006.08.017.
Liu R. et al., "Dopamine as a Carbon Source: The Controlled Synthesis of Hollow Carbon Spheres and Yolk-Structured Carbon Nanocomposites", Angew. Chem. Int. Ed. (2011), 50, pp. 6799-6802 DOI: 10.1002/anie.201102070.
Rosenthal M.W. et al., "Molten-salt reactors—History, status, and potential", Oak Ridge National Laboratory, Oak Ridge, Tennessee 37830 (1969), 12 pages.
Siemer D.D. "Why the molten salt fast reactor (MSFR) is the 'best' Gen IV reactor", Energy Science & Engineering (2015), 3(2), pp. 83-97 doi: 10.1002/ese3.59.
Uhlir J. "Chemistry and technology of Molten Salt Reactors—history and perspectives", Journal of Nuclear Materials (2007), 360, pp. 6-11 doi:10.1016/j.jnucmat.2006.08.008.
Williams D.F. "Assessment of Candidate Molten Salt Coolants for the NGNP/NHI Heat-Transfer Loop", Nuclear Science and Technology Division, Oak Ridge National Laboratory (2006), 44 pages.
Zhang, P., et al., "Recent advances in carbon nanospheres: synthetic routes and applications", The Royal Society of Chemistry, Chem. Commun., 2015, Accepted Apr. 2, 2015, pp. 9246-9256, 51.

\* cited by examiner

*Primary Examiner* — Gary D Harris
(74) *Attorney, Agent, or Firm* — Scully, Scott, Murphy & Presser, P.C.

(57) ABSTRACT

A heat transfer (exchange) composition comprising a halide salt matrix having dispersed therein nanoparticles comprising elemental carbon in the absence of water and surfactants, wherein said halide is fluoride or chloride, wherein the halide salt may be an alkali halide salt (e.g., lithium fluoride, sodium fluoride, potassium fluoride, rubidium fluoride, sodium chloride, potassium chloride, rubidium chloride, and eutectic mixtures thereof) or an alkaline earth halide salt (e.g., fluoride or chloride salt of beryllium, magnesium, calcium, strontium, or barium), and wherein the nanoparticles comprising elemental carbon may be solid or hollow, and wherein the composition may further include nanoparticles comprising a fissile material (e.g., U, Th, or Pu) dispersed within the composition. Molten salt reactors (MSRs) containing these heat transfer compositions in coolant loops in thermal exchange with a reactor core, as well operation of such MSRs, are also described.

23 Claims, No Drawings

MOLTEN SALT COMPOSITIONS WITH ENHANCED HEAT TRANSFER AND REDUCED CORROSION PROPERTIES

CROSS REFERENCE TO RELATED APPLICATION

The present application claims benefit of U.S. Provisional Application No. 62/534,937, filed on Jul. 20, 2017, all of the contents of which are incorporated herein by reference.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention generally relates to molten salt compositions and their use as coolant and heat transfer materials in high temperature applications, such as molten salt reactors.

BACKGROUND OF THE INVENTION

The use of nuclear power is expected to increase due to growing global population and improved standards of living in emerging economies. Nuclear power remains a mature, low carbon source for non-variable baseload electricity generation, and is, therefore, very appealing. Accident tolerance, however, is a growing concern. Molten salt reactors (MSRs) are a class of generation IV nuclear reactors gaining more attention due to their greater accident tolerance by virtue of their use of a liquid coolant or fuel composed of molten metal halides (e.g., Fray, D., *Faraday Discuss.* 2016, 190, 11-34; and LeBlanc, D., *Nucl. Eng. Des.* 2010, 240, 1644-1656). Since high temperatures are required to maintain the liquid phase of the coolant/fuel melt, accident conditions result in passive cooling to ambient temperatures and subsequent coolant/fuel solidification. Moreover, in contrast to the current fleet of light water reactors, water is not required to cool the reactor, which advantageously permits construction of such facilities in areas devoid of extensive aqueous resources.

While the inherent safety of MSRs bestows great potential for future use, the conventional metal halide salt presents some significant problems, including high corrosivity and lower than ideal heat capacity. The high corrosivity requires the use of costly corrosion-resistant materials (e.g., nickel-based hastelloy) for piping used in transporting the molten salt, and even so, regular inspection and maintenance of the transporting apparatus are needed. Turning to the deficiency in heat capacity, it is important to consider that effective heat transfer dictates the efficiency of reactor energy production. Molten salt cooling is used in several reactor concepts, particularly those involving fluoride salts, such as "FLiNaK," a LiF—NaF—KF-based eutectic, or "FLiBe," a LiF—BeF-based eutectic (R. O. Scarlat et al., *Progress in Nuclear Energy* 2014, 77, 406-420). A significant challenge with these salts is the heat capacity, which directly relates to the energy conversion efficiency in converting the reactor heat to water-steam through a series of heat exchangers. If the heat capacity of the salt is not efficient in transferring the reactor core heat to the water for steam production, the efficiency of electricity generation is negatively impacted. Improved heat removal from the core should also result in reduced reactor construction cost, such as by permitting the use of alternative materials that can operate under less stringent code-case qualifications.

SUMMARY OF THE INVENTION

In a first aspect, the present disclosure is directed to compositions useful as molten salt heat transfer materials for high temperature processes, such as encountered in molten salt reactors (MSRs). The compositions disclosed herein have exceptional heat capacities, and thus, exceptional heat transfer abilities, and this, advantageously coupled with a significantly reduced corrosivity compared to conventional molten salts of the art. More particularly, the compositions described herein include a halide salt matrix (e.g., alkali and/or alkaline earth halide salt matrix) having dispersed therein nanoparticles containing elemental carbon (i.e., "carbon nanoparticles") in the absence of water and surfactants, wherein the halide is fluoride or chloride. Generally, the carbon nanoparticles are homogeneously dispersed in a continuous (i.e., non-particulate) matrix of the alkali halide salt. The carbon nanoparticles may be solid or hollow. In some embodiments, the carbon nanoparticles have a core-shell type of structure in which the core is composed of a metal (such as a transition metal or fissile element, such as U, Th, or Pu), which is encapsulated by a carbon shell. Although the compositions are herein described as molten salt compositions, it should be appreciated that the composition may not always be in a molten state, such as when the composition is not in use. The solid composition can be heated so as to revert to a molten state. Thus, the composition described above includes embodiments in which the halide salt matrix is in solid form or liquefied (molten) form.

In a second aspect, the present disclosure is directed to a molten salt reactor (MSR) in which the above-described molten salt composition is incorporated as a heat transfer material. In the MSR, the molten salt may be used as a heat exchange material not in admixture with the fissile material, i.e., the molten salt may be transported in coolant loops that transfer heat from the reactor core in which fissile material is separately located. Alternatively, fissile material may be dispersed within molten salt housed in the reactor core, such that the molten salt can function as both reactor (fissile) material and heat transfer material. In the latter embodiment, the reactor material includes a molten alkali halide salt, or a molten alkaline earth halide salt, or molten combination thereof, and carbon nanoparticles, as described above, along with nanoparticles of the fissile material. The nanoparticles of the fissile material may be uncoated with carbon when in the presence of the carbon nanoparticles, or alternatively, the nanoparticles of the fissile material are coated with a layer of carbon (as described above for core-shell metal-carbon nanoparticles), the latter of which may or may not be in the presence of separate carbon nanoparticles dispersed in the molten salt. The present disclosure is also directed to the operation of an MSR containing the molten salt composition described above.

DETAILED DESCRIPTION OF THE INVENTION

In a first aspect, the present disclosure is directed to a heat transfer composition that contains a halide salt composition as a continuous (i.e., non-particulate) matrix in which nanoparticles containing elemental carbon (i.e., carbon nanoparticles) are dispersed. Generally, the carbon nanoparticles are homogeneously dispersed throughout the halide salt matrix. The carbon nanoparticles should contain carbon at least on the surfaces of the nanoparticles, i.e., the nanoparticles may or may not contain a core other than carbon, along with a carbon shell encapsulating the core. Thus, there should exist a carbon-halide salt interface between the carbon nanoparticles and halide salt matrix.

In some embodiments, the halide salt is or includes one or more alkali halide salts. The alkali halide is typically an alkali fluoride or alkali chloride. The alkali metal may be, for example, lithium (Li), sodium (Na), potassium (K), or rubidium (Rb), or some combination thereof. Some examples of alkali fluorides include lithium fluoride, sodium fluoride, potassium fluoride, and rubidium fluoride. Some examples of alkali chlorides include lithium chloride, sodium chloride, potassium chloride, and rubidium chloride.

In other embodiments, the halide salt is or includes one or more alkaline earth halide salts. The alkaline earth halide is typically an alkaline earth fluoride or alkaline earth chloride. The alkaline earth metal may be, for example, beryllium (Be), magnesium (Mg), calcium (Ca), strontium (Sr), barium (Ba), or some combination thereof. Some examples of alkaline earth fluorides include beryllium fluoride, magnesium fluoride, calcium fluoride, and strontium fluoride. Some examples of alkaline earth chlorides include beryllium chloride, magnesium chloride, calcium chloride, and strontium chloride.

In some embodiments, the halide salt composition (matrix) contains one alkali halide salt (e.g., solely LiF, LiCl, NaF, or NaCl), which may or may not be admixed with one or more non-alkali halide salts, such as an alkaline earth metal salt (e.g., $BeF_2$, $MgF_2$, or $CaF_2$), main group metal salt (e.g., $AlF_3$), transition metal salt (e.g., $ZrF_4$), or fissile metal salt (e.g., $UF_4$), or combination thereof. In other embodiments, the halide salt composition (matrix) contains two or more alkali halide salts, typically as a eutectic, e.g., a LiF—NaF, LiF—NaF—KF, LiF—BeF, LiCl—NaCl, or LiCl—NaCl—KCl mixture, which may or may not be admixed with one or more non-alkali halide salts, such as an alkaline earth metal salt, main group metal salt, transition metal salt, or fissile metal salt, or combination thereof. In similar fashion, the halide salt composition may contain one alkaline earth halide salt, or two or more alkaline earth halide salts, and the one or two alkaline earth halide salts may or may not be admixed with one or more non-alkaline earth halide salts, such as an alkali halide salt, main group metal salt, transition metal salt, or fissile metal salt, or combination thereof. The term "main group metal," as used herein, generally refers to Groups 13, 14, and/or 15 of the Periodic Table. The term "transition metal," as used herein, generally refers to Groups 3-12 (or sub-grouping therein, e.g., Groups 3-5 or 3-6) of the Periodic Table. The halide salt matrix may or may also include a non-halide salt, such as an alkali nitrate (e.g., $LiNO_3$, $NaNO_3$, or $KNO_3$), alkali carbonate (e.g., $Li_2CO_3$, $Na_2CO_3$ or $K_2CO_3$), or alkaline earth carbonate (e.g., $MgCO_3$ or $CaCO_3$). Generally, the halide salt composition (matrix) has a melting point of at least or above, for example, 600° C., 650° C., 700° C., 750° C., 800° C., or 850° C., or a temperature within a range bounded by any two of the foregoing temperatures.

The nanoparticles containing elemental carbon (i.e., carbon nanoparticles) are dispersed, preferably homogeneously, within the alkali halide matrix. The term "elemental carbon," as used herein, refers either to carbon in a formal zerovalent state or in a metal carbide state. The carbon nanoparticles may be solid or hollow. Some examples of carbon nanoparticles containing carbon in the zerovalent state include exfoliated graphite nanoplatelets, spherical fullerenes (e.g., buckminsterfullerene, e.g., $C_{60}$ as well as any of the smaller or larger buckyballs, such as $C_{20}$ or $C_{70}$), tubular fullerenes (e.g., single-walled, double-walled, or multi-walled carbon nanotubes), carbon black ("CB"), carbon nanodiamonds, carbon onions, carbon nanobuds, carbon nanofibers (e.g., vapor grown), graphene oxide nanoparticles, and reduced graphene oxide nanoparticles. All of the foregoing types of carbon nanoparticles are well known in the art. For example, exfoliated graphite nanoplatelets are described in detail in, e.g., J.-H. Ding et al., *Scientific Reports,* 8, 5567, 2018; graphene oxide nanoparticles are described in detail in, e.g., J.-L. Li et al., *Angew. Chem. Int. Ed.,* 51(8), 1830-1834, 2012; reduced graphene oxide nanoparticles are described in detail in, e.g., S. N. Alam et al., *Graphene,* 6(1), January 2017; and carbon nanofibers are described in detail in, e.g., M. H. Al-Saleh et al., *Composites Part A: Applied Science and Manufacturing,* 42(12) 2126-2142, December 2011. Some examples of metal carbide nanoparticles include nanoparticles of silicon carbide (SiC), titanium carbide (TiC), tungsten carbide (WC), and aluminum carbide ($Al_4C_3$). In some embodiments, the carbon nanoparticles are functionalized with one or more types of heteroatoms (e.g., F, Cl, O, and/or N) to make the carbon nanoparticles further compatible with, and hence, further dispersible in, the halide salt matrix. The heteroatoms may be present in the form of functional groups on the surface of the carbon nanoparticles, such as hydroxy, carboxy, and/or amine groups. The carbon nanoparticles generally have a particle size of up to or less than 200, 500, or 1000 nm in at least one or two of its dimensions. In different embodiments, the nanoparticles have a size (or average size) of up to or less than, for example, 500 nm, 250 nm, 200 nm, 150 nm, 100 nm, 50 nm, 20 nm, 10 nm, or 5 nm, or a size within a range bounded by any two of the foregoing particle sizes.

In particular embodiments, the carbon nanoparticles are hollow. The hollow carbon nanoparticles may be, for example, spherical fullerenes, such as buckminsterfullerene, which has a diameter of approximately 1 nm. Larger hollow carbon nanoparticles, other than the fullerenes, and typically of 20-500 nm diameter, are also well known in the art. Such hollow nanoparticles are described in, for example, Z.-C. Yang et al., *Chem. Mater.,* 25(5), 704-710, 2013; H. Zhang et al., *Chem. Mater.,* 27(18), 6297-6304, 2015; Q. Wang et al., *Carbon,* 52, 209-218, February 2013; Z. Han et al., *Synthetic Metals,* 187, 91-93, January 2014; and J. Wutthiprom et al., *ACS Omega,* 2(7), 3730-3738, 2017, all of the contents of which are incorporated herein by reference.

Generally, the carbon nanoparticles are included in the heat transfer composition in an amount of at least 0.1 and up to 10 wt % (i.e., by weight of all salts and carbon nanoparticles included in the heat transfer composition). In different embodiments, the carbon nanoparticles are included in the heat transfer composition in an amount of about, at least, or above, for example, 0.1, 0.2, 0.5, 1, 2, 3, 4, 5, 6, 7, 8, 9, or 10 wt %, or an amount within a range bounded by any two of the foregoing values. The carbon nanoparticles can be alternatively included in corresponding volume amounts, such as an amount of at least or above 0.1, 0.2, 0.5, or 1 vol % and up to 1.5, 2, 2.5, 3, 4, or 5 vol %.

As mentioned above, the carbon nanoparticles need not be composed of carbon throughout the nanoparticle, as long as the nanoparticle is composed of carbon or a metal carbide at least on surfaces of the nanoparticles. Thus, in some embodiments, the carbon nanoparticle may have a core-shell structure in which a core portion of the nanoparticle is composed of or includes a non-carbon element (e.g., a transition metal or fissile element) and the core portion is surrounded (encapsulated) by a shell of carbon. The transition metal may be a first row, second row, or third row transition metal, either in its metallic state or a non-metallic state, such as in a transition metal oxide. In some embodiments, a transition metal having catalytic properties at elevated temperatures (e.g., capability of facilitating a petrochemical conversion reaction) is selected to be in the core portion. In the case of the core portion being composed of or including a fissile element, the fissile element may be, for example, U, Th, or Pu. The latter fissile elements are typically in the form of their oxides or halides. A shell of carbon can be deposited on metal-containing nanoparticles by means known in the art, such as by the deposition of dopamine followed by carbonization, such as described in, for example, R. Liu et al., *Angew. Chem. Int. Ed.*, 50, 6799-6802, 2011, the contents of which are herein incorporated by reference.

In some embodiments, the heat transfer composition further includes nanoparticles composed of or including a fissile material, wherein the nanoparticles of the fissile material are dispersed within the alkali halide salt matrix. The nanoparticles of the fissile material may contain, for example, U, Th, or Pu, typically as oxides or halides of these elements. In some embodiments, the nanoparticles of fissile material are coated with carbon. In the latter case, the carbon-coated fissile nanoparticles function as carbon nanoparticles; thus, the carbon-coated fissile nanoparticles may or may not be admixed with carbon nanoparticles that are homogeneously carbon. In other embodiments, the nanoparticles of fissile material are not coated with carbon, in which case the nanoparticles of fissile material are necessarily admixed with carbon nanoparticles. The nanoparticles of fissile material can have any of the sizes provided above for the carbon nanoparticles.

For purposes of the present invention, the heat transfer composition described above does not include water or surfactants. The surfactants being excluded from the above-described composition include organic and inorganic surfactants, wherein it is understood that surfactants function to modify interactions between two phases (in the present case, carbon nanoparticles and alkali halide matrix) such that one phase (e.g., carbon) is maximally dispersed in stable form in the other phase (e.g., alkali halide). Such compounds that are surface active at interfaces are unnecessary for purposes of the present invention, and in any event, would likely carbonize at the high temperatures at which these heat transfer compositions are used. Some examples of surfactants include various gums (e.g., gum arabic), sodium dodecyl sulfate, fatty acid salts, siloxanes, and polysiloxanes, all of which are excluded from the heat transfer composition described herein.

In other aspects, the present disclosure is directed to molten salt reactors (MSRs) containing the above-described heat transfer composition, as well as methods for operating such MSRs. As well known in the art, an MSR contains a reactor core in which fissile material is housed and undergoes fission for energy production. As indicated earlier above, and as further discussed below, the above-described halide salt heat transfer composition can be separate from the fissile material, or alternatively, the heat transfer composition can include fissile material as a component. The design, construction, and operation of MSRs is well known in the art and has a long history, such as detailed in, for example, J. Uhlir, *Journal of Nuclear Materials*, 360, 6-11, 2007; D. LeBlanc, *Nuclear Engineering and Design*, 240, 1644-1656, 2010; and D. D. Siemer, *Energy Science and Engineering*, 3(2), 83-97, 2015, all of the contents of which are herein incorporated by reference.

In particular embodiments, a coolant loop (generally, a primary coolant loop) containing any of the above-described heat transfer compositions is positioned within sufficient proximity to the reactor core of an MSR so as to remove (transfer) heat from the reactor core to the coolant loop, thereby maintaining the reactor core within a safe operating temperature. As discussed above, the heat transfer composition contains a matrix composed of at least one alkali halide salt, and nanoparticles containing elemental carbon dispersed within the alkali halide salt matrix, wherein the carbon nanoparticles can have a single phase composition or a core-shell structure in which a metal (e.g., a transition metal or fissile element) is within a core and a carbon shell surrounds the core. As also discussed above, the heat transfer material may or may not additionally include nanoparticles of a fissile material that is uncoated. Often, the primary coolant described above is also within sufficient proximity to a secondary coolant loop so as to permit the secondary coolant loop to remove (transfer) heat from the primary coolant loop to the secondary coolant loop. The secondary coolant loop may contain any flowable material useful as a secondary heat transfer material in a nuclear reactor. Some examples of secondary coolant loop materials include water, supercritical carbon dioxide, and low melting salts, e.g., ionic liquids and quaternary ammonium and phosphonium salts. As the carbon nanoparticles in the heat transfer composition described herein have been found to substantially reduce corrosivity of the halide salts, the MSR may employ a more common and less costly material in place of nickel-based hastelloy materials for inner walls of the coolant loop. For example, stainless steel, which is significantly less costly, may be used as a material for the coolant loop holding the heat transfer material described herein.

In embodiments where fissile material is included in the heat transfer material, the heat transfer material also functions as reactor (fissile) material. In the latter case, the primary coolant loop may be flowably connected to (and an extension of) the reactor. Such a reactor design is also herein referred to as a "liquid-fuel reactor". Liquid-fuel reactors are considered as "accident tolerant" alternatives to the light-water reactors currently in widespread use. This is due to the ability to solidify the fuel and stop the fission reaction by simply lowering the salt temperature below the solidification point. There are significant challenges with the conventional model, however, that have precluded widespread commercial use. As indicated earlier, corrosion of reactor components is the primary challenge. The liquid fuels are typically halide salts, e.g. chloride or fluoride, which are moisture sensitive and highly corrosive when loaded with dissolved uranium halide nuclear fuel. This is a roadblock for reactor development as new corrosion resistant materials must be developed and undergo very expensive code qualification for use in reactors.

The present invention has improved on the liquid-fuel reactor concept by either dispersing carbon nanoparticles in a molten halide salt matrix in admixture with fissile particles or by coating fissile particles with carbon. In the foregoing embodiments, the carbon coating (or presence of carbon nanoparticles) substantially reduces or prevents aggregation and sintering. Corrosivity of the molten salt is driven by the reduction of $UX_4$ (X=Cl, F) to $UX_3$, which results in oxidation of the reactor components that it contacts. Most traditional metal oxide layers form flakes or are readily dissolved, such as ferrous oxide, commonly observed as rust. Use of fissile nanoparticles reduces the surface area of the uranium species, which decreases contact of the uranium species with reactor components, thereby impeding the corrosion. The carbon coating serves as a passive layer that further inhibits electron transfer to the uranium species, thereby further inhibiting corrosion. This lack of corrosivity advantageously permits the use of less expensive and more common metals for the reactor components, thereby lowering construction costs and decreasing construction leadtime.

The development of porous hard carbon spheres possessing tunable diameters and readily accessible interior void volumes have been reported (R. Liu et al., *Angew. Chem. Int. Ed.*, 50, 6799-6802, 2011). These and other rigid carbon spheres can be added to dissolved uranium (or other fissile) solutions, allowing diffusion of the uranium into the interior of the carbon sphere. Alternatively, uranium oxide nanocrystals can be synthesized (Wu, H. M., et al., *Journal of the American Chemical Society* 2006, 128, 16522-16523) and then coated with a carbon shell, such as the dopamine-based carbon shell described in Liu et al. (supra). Nanoparticles of other fissile materials (e.g., thorium oxide or plutonium oxide) may be synthesized by similar methods, and similarly coated with carbon, if desired.

An added benefit to the development of nanoparticle-based fuels in molten salts is the ability to utilize the readily available uranium(VI) oxidation state without deleterious effect on reactor integrity. As discussed above, the reduction of $UX_4$ to $UX_3$ drives corrosion issues, yet the comparative ease of large-scale preparation of the $UX_4$ molecule from gaseous $UF_6$ required for isotopic enrichment is what induces its preferential use in molten salt reactors. Nevertheless, preparation of $UX_4$ involves formation of gaseous uranium and reaction with highly toxic and corrosive gases. In contrast, uranium (VI) is environmentally abundant as the $UO_2^{2+}$ ("uranyl") cation, but would be rapidly reduced in a molten salt, oxidizing three times as many metals as $UX_4$ and accelerating corrosion in the melt. An overall insolubility of $UO_2^{2+}$ in chloride salts has also been demonstrated, which would prevent uniform diffusion and transport. By forming uranyl nanoparticles with carbonaceous coatings, the corrosive properties can be simultaneously inhibited, as discussed above, and the cost and hazard associated with producing nuclear fuel for molten salt reactors can also be decreased.

The current discussion has been focused on uranium-based fuels, as uranium is the primary choice for fuels in the United States. Nevertheless, the technology discussed herein is applicable to other nuclear fuels as well. For example, thorium-based fuels are becoming popular in liquid-fuel reactors due to the prevalence of thorium relative to uranium and mixed oxide fuels (MOX), which is a blend of depleted uranium (U-238) and plutonium (Pu-239), used to generate power.

Examples have been set forth below for the purpose of illustration and to describe certain specific embodiments of the invention. However, the scope of this invention is not to be in any way limited by the examples set forth herein.

Examples

Synthesis of Heat Transfer Compositions Containing Hollow Carbon Nanospheres

Magnesium chloride, due to its hygroscopic nature, was purified by distillation and kept in oxygen and a water-free glovebox. Distillation was performed under vacuum at 800° C. in a Watlow ceramic fiber heater. Potassium and sodium chlorides were purified by carbochlorination using sparging with $CCl_4$ at elevated temperatures. Carbon particles were used as received.

In a standard experiment, 2-5 mg of hollow carbon spheres (i.e., "HCS," generally, about 200-250 nm in diameter) were loaded into a quartz tube and sealed with a valve with two ACE threads, one connecting to the tube and the other to the Schlenck line, to establish air-free conditions. After air was evacuated, the sealed tube was taken into the glovebox and 1 g of salts was added to it. The salt composition included pure $MgCl_2$, $MgCl_2$ and KCl (with 60 and 30 mol % of $MgCl_2$) mixtures, as well as $MgCl_2$ and NaCl (with 30 mol % $MgCl_2$) mixtures. The tube was then heated to 800° C., and the resulting molten salt/carbon mixture was visually examined. After two hours, the salt was cooled down and transferred into the glovebox to be used in further studies with differential scanning calorimetry (DSC) for heat capacity and melting point analyses.

Analysis of the Heat Transfer Compositions

The best dispersion of carbon particles in the salt mixture was achieved with hollow carbon spheres. Notably, the carbon particles turned bright red in color in the furnace and then slowly turned black, at which time they were removed from the furnace for inspection. The color change was found to be due to black body radiation of the particles that had a higher local temperature than the salt. This color change works as a very good qualitative tool to determine whether particles are dispersed in the salt. Based on these observations, HCS of various wall thicknesses (20-200 nm) disperse in the molten salt under argon, and disperse even more after applying vacuum, due to displacement of the atmosphere in the particles by the salt. Other particles either sedimented or floated in the salt or reacted with it (OLC/MnOx, i.e., onion-like carbon/mangenese oxide core-shell nanoparticles).

After it was established that HCS have better dispersion capabilities, further experiments were conducted with them in mixtures of $MgCl_2$ and KCl (or NaCl). Addition of KCl reduced the concentration of particles in the salt mix under argon atmosphere. However, applying a vacuum helped disperse more particles. It should be noted that mixtures with an excess of KCl had a lower concentration of particles even after evacuation. The same trend was observed in the mixtures with NaCl, which indicates that the dispersivity is dependent on the acidity of the salt and not the ionic size of cations in the molten salt.

While there have been shown and described what are at present considered the preferred embodiments of the invention, those skilled in the art may make various changes and modifications which remain within the scope of the invention defined by the appended claims.

What is claimed is:

1. A composition comprising a halide salt matrix having dispersed therein nanoparticles comprising elemental carbon in the absence of water and surfactants, wherein said halide salt is an alkali halide salt, alkaline earth halide salt, or combination thereof, and said halide is fluoride or chloride.

2. The composition of claim 1, wherein said halide salt contains at least one alkali halide salt selected from the group consisting of lithium fluoride, sodium fluoride, potassium fluoride, rubidium fluoride, sodium chloride, potassium chloride, rubidium chloride, and eutectic mixtures thereof.

3. The composition of claim 1, wherein said nanoparticles comprising elemental carbon are selected from the group consisting of hollow carbon nanospheres, exfoliated graphite nanoplatelets, carbon nanotubes, spherical fullerenes, carbon black, carbon nanodiamonds, carbon onions, carbon nanofibers, graphene oxide nanoparticles, reduced graphene oxide nanoparticles, and metal carbide nanoparticles.

4. The composition of claim 1, wherein said composition further comprises nanoparticles comprising a fissile material dispersed within said composition.

5. The composition of claim 4, wherein said fissile material comprises uranium, thorium, or plutonium.

6. The composition of claim 1, wherein said nanoparticles comprising elemental carbon contain a core of a metal encapsulated by a shell of carbon.

7. The composition of claim 6, wherein said metal is a fissile material.

8. The composition of claim 7, wherein said fissile material comprises uranium, thorium, or plutonium.

9. A molten salt reactor comprising (i) a reactor core in which fissile material is housed and (ii) a coolant loop containing a molten salt composition, wherein said coolant loop is within sufficient proximity to said reactor core so as to remove heat from said reactor core and maintain said reactor core within a safe operating temperature, and wherein said molten salt composition comprises a halide salt matrix having dispersed therein nanoparticles comprising elemental carbon in the absence of water and surfactants, wherein said halide salt is an alkali halide salt, alkaline earth halide salt, or combination thereof, and said halide is fluoride or chloride.

10. The molten salt reactor of claim 9, wherein said coolant loop is a primary coolant loop.

11. The molten salt reactor of claim 10, wherein said primary coolant loop is within sufficient proximity to a secondary coolant loop so as to permit said secondary coolant loop to remove heat from said primary coolant loop.

12. The molten salt reactor of claim 11, wherein said secondary coolant loop contains water or supercritical carbon dioxide.

13. The molten salt reactor of claim 9, wherein walls of said coolant loop in contact with the molten salt are constructed of stainless steel.

14. The molten salt reactor of claim 9, wherein said halide salt contains at least one alkali halide salt selected from the group consisting of lithium fluoride, sodium fluoride, potassium fluoride, rubidium fluoride, sodium chloride, potassium chloride, rubidium chloride, and eutectic mixtures thereof.

15. The molten salt reactor of claim 9, wherein said nanoparticles comprising elemental carbon are selected from the group consisting of exfoliated graphite nanoplatelets, carbon nanotubes, spherical fullerenes, carbon black, carbon nanodiamonds, carbon onions, carbon nanofibers, graphene oxide nanoparticles, reduced graphene oxide nanoparticles, and metal carbide nanoparticles.

16. The molten salt reactor of claim 9, wherein said composition further comprises nanoparticles comprising a fissile material dispersed within said composition.

17. The molten salt reactor of claim 16, wherein said fissile material comprises uranium, thorium, or plutonium.

18. The molten salt reactor of claim 9, wherein said nanoparticles comprising elemental carbon contain a core of a metal encapsulated by a shell of carbon.

19. The molten salt reactor of claim 18, wherein said metal is a fissile material.

20. The molten salt reactor of claim 19, wherein said fissile material comprises uranium, thorium, or plutonium.

21. The composition of claim 1, wherein said nanoparticles comprising elemental carbon are hollow carbon nanospheres.

22. The composition of claim 1, wherein said halide salt matrix contains a combination of an alkali halide salt and alkaline earth halide salt.

23. The composition of claim 1, wherein said composition excludes carbon nanotubes.

* * * * *